United States Patent [19]

Knospler

[11] 4,226,121
[45] Oct. 7, 1980

[54] ULTRASONIC IMAGING SYSTEM AND IMPROVED SIGNAL PROCESSOR THEREFOR

[76] Inventor: William M. Knospler, Fenwick Rd., Rte. 206, Augusta, N.J. 07822

[21] Appl. No.: 16,873

[22] Filed: Mar. 2, 1979

[51] Int. Cl.$^2$ ........................................... G01N 29/04
[52] U.S. Cl. ........................................ 73/602; 73/620
[58] Field of Search ............... 73/602, 613, 618, 620, 73/642; 128/660; 328/143, 127, 163, 164; 307/268, 229

[56] References Cited

U.S. PATENT DOCUMENTS 3,565,057  2/1971  Hart ...................................... 73/620
4,016,750  4/1977  Green ................................... 73/620

Primary Examiner—Anthony V. Ciarlante
Attorney, Agent, or Firm—Lane, Aitken, Ziems, Kice & Kananen

[57] ABSTRACT

In an ultrasonic imaging system, a signal processor is provided which converts the portions of the received signal representing sonic reflections to more closely resemble the acoustic impedance changes which generated the reflections. The signal processor differentiates the received signal after demodulation and the differentiated signal is added to the received demodulated signal delayed by one-half cycle of the ripple frequency of the ultrasonic pulses.

11 Claims, 4 Drawing Figures

ULTRASONIC IMAGING SYSTEM AND IMPROVED SIGNAL PROCESSOR THEREFOR

This invention relates to ultrasonic imaging systems, and more particularly, to such a system with an improved signal processor which greatly improves the quality of the image produced by the system. Ultrasonic image equipment is widely used as a diagnostic tool by way of providing images of acoustic impedance changes within the human body. Because such acoustic image changes represent boundary conditions in organ structure, the images produced are of the boundaries and interfaces within the body being scanned by the equipment.

The images that are produced by the diagnostic equipment of the prior art are quite fuzzy and are incapable of resolving fine detail. When boundary conditions or interfaces occur in closely spaced relationships, false images are produced and the images have a filled in appearance.

The system of the present invention greatly improves the quality of the image produced by providing much higher resolution and produces an image which is crisper, more detailed and more complete than was heretofore possible.

The present invention achieves the improved results by eliminating undesirable artifacts in the signals produced by the ultrasonic pulses. In the systems of the prior art, ultrasonic pulses are focused to improve lateral resulution. The focusing causes a curvature in the acoustic wave, which contributes to reflection signals which have gradual rise and fall times, even though the reflections are caused by abrupt changes in acoustic impedance. In addition, the pulses which represent reflections have a ripple superimposed on their amplitude caused by the fact that the ultrasonic pulses have a carrier frequency and the ulstrasonic pulses extend for several cycles of this carrier frequency. This ripple cannot be filtered out without sacrificing system bandwidth and resulting in further image degradation.

SUMMARY OF THE PRESENT INVENTION

The present invention provides a signal processor which converts the signal pulses representing reflections and having gradual rise and fall times to step functions having steep rise and fall times and at the same time substantially eliminates the ripple without affecting the bandwidth of the system. In accordance with the present invention, the received signal after conventional demodulation and compression is differentiated and then added to the original process signal delayed by one-half cycle of the ripple frequency. The resulting signal pulses representing reflections are step functions with steep rise and fall times and with very little ripple.

DETAILED DESCRIPTION OF THE PRESENT INVENTION

Figure 1:
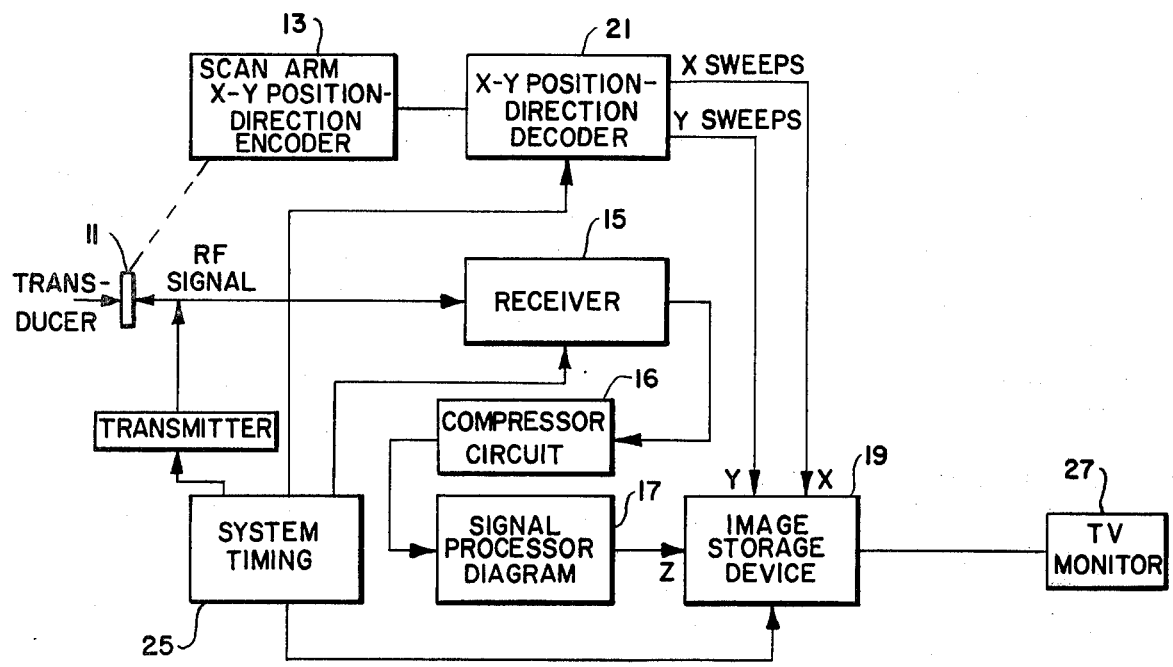
FIG. 1 is a block diagram illustrating an ultrasonic imaging system with the improved signal processor of the present invention.

As shown in FIG. 1, the ultrasonic pulse echo display system of the present invention comprises a transducer 11, which transmits high frequency ultrasonic pulses into the body of the subject. The pulses typically have a frequency in the range of from 1 to 10 MHz and are controlled by timing system 25. The pulses each cause an acoustic wave to travel through the body of the subject and the acoustic wave is reflected by acoustic impedance changes in the body back to the transducer where the reflections are detected and converted into an electrical signal. The transducer is mounted on a scanning arm and as the pulses are transmitted, the direction that the pulse is transmitted and the position of the transmitter is varied so that the path of the transmitted pulse varies in a predetermined plane. Some energy from the transmitted acoustic pulse will be reflected each time the pulse encounters a change in acoustic impedance which will correspond to a change in tissue characteristics. The amplitude of each reflection is directly related to the difference between the acoustic impedances at the boundary point and the amplitude of the incident pulse as it encounters the boundary point. The signal generated by the transducer in response to the resulting reflected waves is applied to a receiver circuit 15 which amplifies the signal, applies time and gain correction to the signal, and amplitude demodulates the signal. The amplitude of the acoustic pulse decreases as it travels forwardly along its path and the signal is adjusted for this decrease in amplitude and for the corresponding decrease in amplitude in the echos during the return trip to the transducer so as to give more or less equal amplitude to the signal portions of the represented echos from equal tissue conditions regardless of the depth from which they come. This correction is provided in the receiver circuit 15. The range of echo amplitudes that can be expected to arise from anatomical structures within the body and considered to be of diagnostic value is 30 DB to 40 DB. In order to handle this range of amplitudes, most systems normally compress the signal such as in a logarithmic function. This compression is carried out by compression circuit 16 which receives the output signal of the receiver 15.

The resulting output of the signal of the compression circuit is applied to a signal processor 17 which constitutes the improvement of the present invention. The processor 17 processes the signal to make the portions of the signal representing reflections of the acoustic wave more closely resemble the acoustic impedance changes that gave rise to the reflections of the acoustic wave, or, in other words, make the portions of the electrical signal representing reflections more closely resemble step functions. The output of the signal processor 17 is applied to an image storage device 19 which stores the applied signal. The image storage device scales the signal for standard video requirements for television monitoring so that amplitudes can be displayed as shades of grey between a near black background for the very weakest echos to a near full white for the very strongest echos. The opposite shade sense may also be used in the video image.

The image storage device 19 is controlled by X and Y sweep signals and stores a record of the amplitude of the applied signal distributed in the storage device so that the positions of the portions of the signal corresponding to reflections are stored at locations in the image storage device corresponding to the locations of the changes in acoustical impedance which gave rise to the reflections. The X and Y sweep signals are generated by an X and Y position direction decoder 21 under the control of the scan arm XY position direction encoder 13 and in response to timing signals from the timing source 25. In response to the representations of the transducer position and the direction in which the transducer transmits pulses, the decoder generates the X and Y sweep signals to correspond to the path along which the ultrasonic pulses are transmitted, one sweep signal being generated for each transmitted pulse. As the position of the transducer and the direction in which the pulses transmitted by the transducer is varied by the operator, signals are generated and stored in the image storage device so that a video image of the acoustic impedance changes is stored in the image storage device. The image will represent the acoustic impedances in cross-section through the body along the plane through which the transmitted pulses are scanned by movement of the position and direction of the transducer 11 by means of the scan arm. The image will be a grey-scale image representing the amplitude of the signal, as generated by the reflections. This amplitude of each portion of the signal corresponding to a reflection will depend upon the character of the acoustic impedance causing the reflection. The acoustic impedances which generate the reflections are, for the most part, interfaces or boundaries between tissue structures and, thus, the grey-scale image will be of interfaces or boundaries between tissue structures. The image stored on the image storage device is transmitted to a TV monitor 27 where it is displayed. The above described system, except for the signal processor 17, is conventional in ultrasonic imaging systems.

Figure 2:
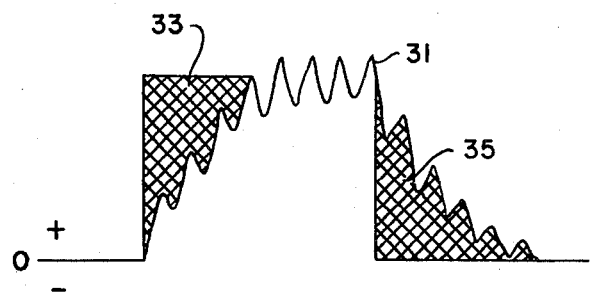
FIG. 2 is an illustration of a typical waveform representing a reflection after conventional processing by the receiver of the ultrasonic imaging system.

The function of the processor 17 is to eliminate undesirable artifacts in the portions of the signal representing reflections. As shown in FIG. 2, a waveform representing a reflection has two artifacts which degrade the image accuracy and completeness. The detected signals' rise time and fall time encompasses several half-cycle durations of the carrier signal which is inherent in the method of generating the signal. On the other hand, the acoustic impedance change that gives rise to the reflected signal resembles a step function. For example, at a point where some body fluid meets the wall of a duct or vessel containing it, the profile of the acoustic impedance at that boundary point is a step function. Accordingly, it would be preferable for the signal to have a steep rise time instead of a rise time lasting over several cycles. In addition, the signal should have a steep fall time. The second artifact is that the detected signal contains a substantial ripple caused by the carrier frequency. This ripple signal, which will be at twice the carrier frequency as a result of the amplitude demodulation in the receiver, does not represent any tissue conditions, but it cannot be filtered off without sacrificing system bandwidth and resulting in further image degradation.

The signal processor 17 deals with both of the above described artifacts simultaneously. The processor corrects the rise and fall time of the echo signal to more nearly represent the acoustic impedance change which created it and, furthermore, it cancels a large part of the ripple contamination without lowering the system bandwidth.

The reason that the signal representing a reflection has a gradual rise and fall time is that the acoustic reflections themselves have gradual rise and fall times, which are caused in part by the shape of the acoustical pulses transmitted by the transmitter. An acoustical pulse typically will have a circular cross section with a power density across the pulse which is gaussian in nature. The pulse diverges as it travels; the more divergent the pulse becomes, the poorer its lateral resolution and the lower its power density becomes. Transducers used in diagnostic ultrasound systems to reduce the problem of this divergence are focused to produce pulses of narrow cross-section and little divergence over the depth of interest. This is achieved by inserting an acoustic lens in the transducer. The acoustic lens creates the acoustic equivalent of a spherical aberation in the pulses and the resulting wavefront of each pulse assumes some degree of the curvature. The wavefront is thereafter distorted and dispersed in an unpredictable way by the effects of absorption, refraction, reflection, and scattering as it passes through the heterogenous tissue substances. As the wavefront of the pulse passes through an acoustic interface, the amount of energy instantaneously reacting with the interface varies with the instantaneous geometric intersection of the wavefront to the interface. This valve additionally reflects the effects of the gaussian power density, any phase cancellation points that lie on the instantaneous line of intersection, and the acoustic characteristics of the interface area. The reflection process continues in time, and varies in phase, until the acoustic pulse has passed completely through the interface. This can last for several diminishing cycles of the carrier frequency.[1] The reflected wave is further acted upon by absorption, refraction, reflection and scattering as it returns to the transducer. All of these factors contribute to a reflection which rises over several carrier half-cycles, lingers at a final value and then falls over several carrier half-cycles. This rise and fall time amounts to a degradation of the depth resolution.

[1] McMaster, *Non-Destructive Testing Handbook*, New York Ronald Press, 1959, pp. 4413–4414.

The system of the invention comprising the signal processor 17, in effect, corrects the gradual rise and fall of the signal. How the system accomplishes this as well as cancelling a large part of the ripple is illustrated in the diagram of a typical waveform representing a reflection shown in FIG. 2. As shown in FIG. 2, the waveform can be converted into a step wave by adding the cross hatched portion 33 to the waveform and removing the cross hatched portion 35. The processor 17 serves to automatically add to each reflection waveform a portion corresponding to the cross hatched portion 33 and automatically subtract from each reflection waveform a portion corresponding to cross hatched portion 35. This is accomplished by the circuit shown in FIG. 3 which illustrates the details of the signal processor 17.

Figure 3:
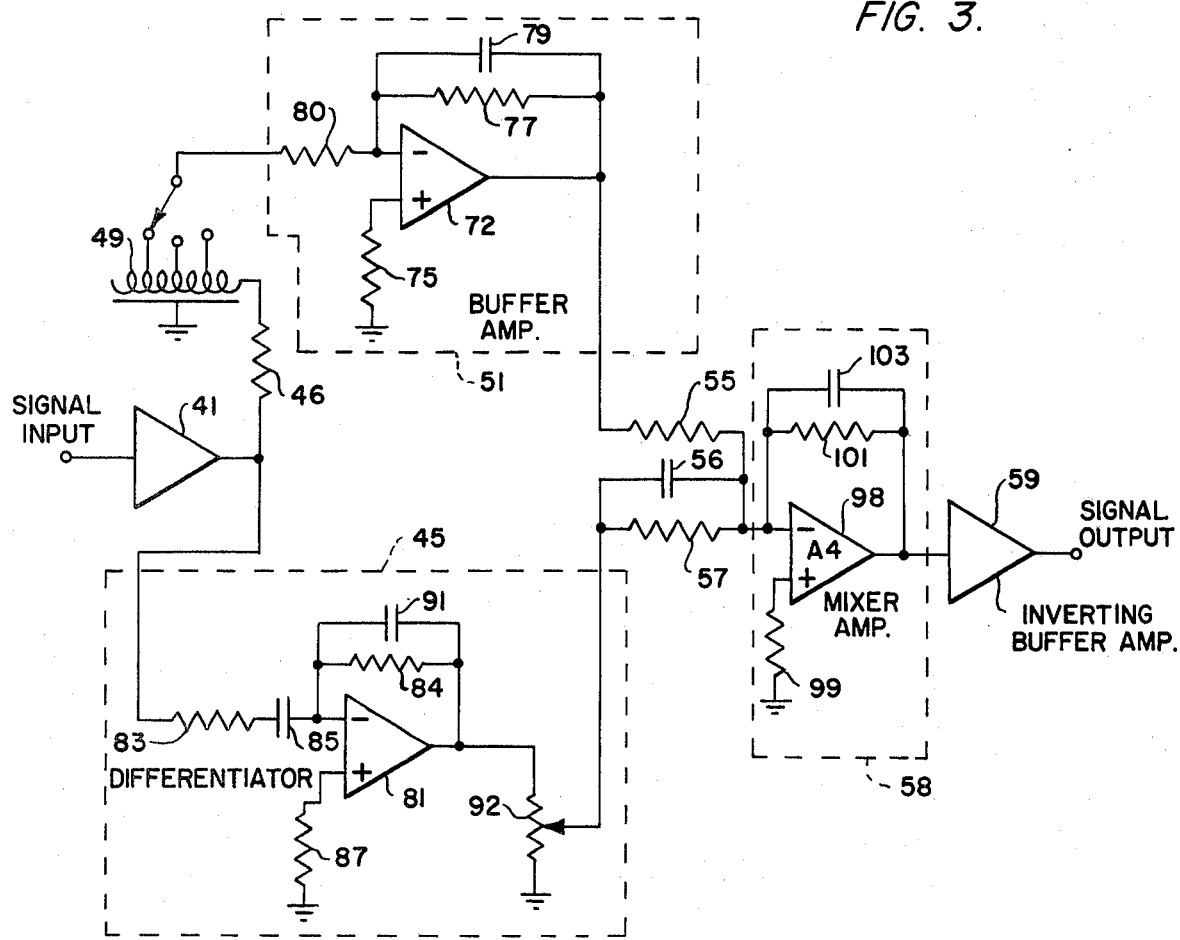
FIG. 3 is a circuit diagram illustrating the improved signal processor of the present invention.
Figure 4:
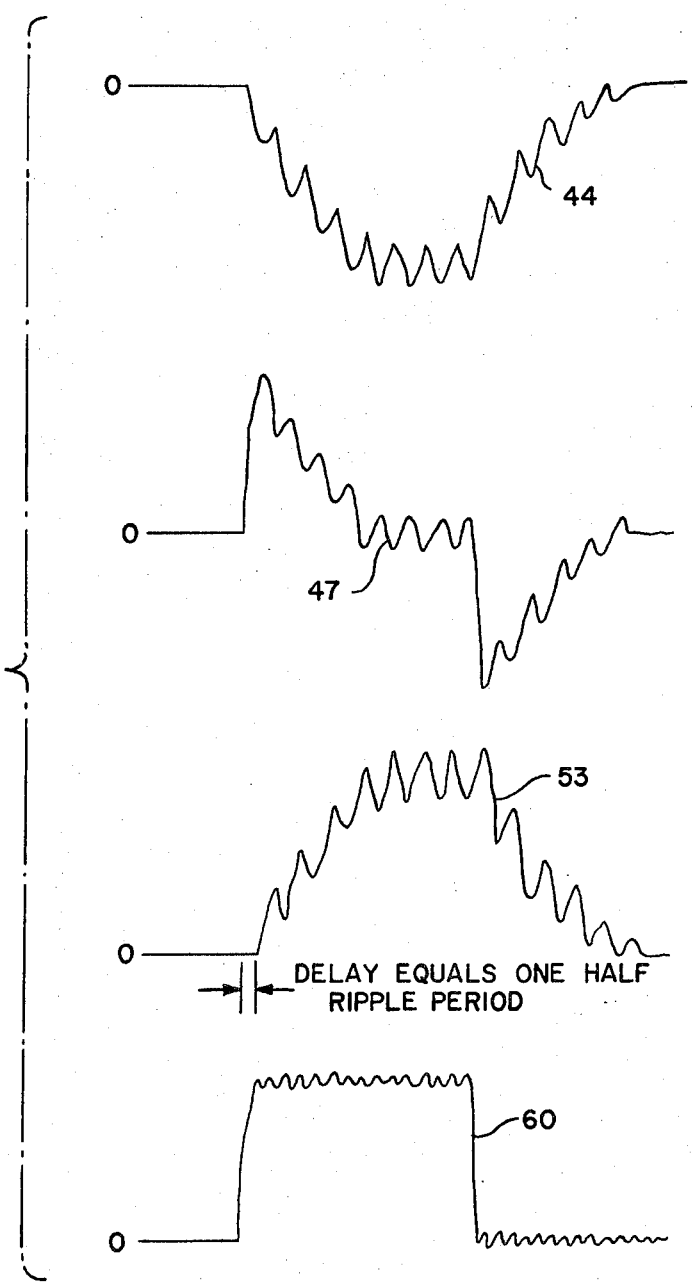
FIG. 4 illustrates waveforms produced in the improved signal processor of the present invention.

As shown in FIG. 3, the signal from the compression circuit 16 including waveforms like that shown in FIG. 2, is applied to an inverting buffer amplifier 41. As a result, a typical reflection signal at the output of the amplifier 41 will have the shape of waveform 44 shown in FIG. 4. The output of the amplifier 41 is applied to a differentiator 45 to produce from the waveform 44 the differentiated signal waveform 47 at the output thereof. In addition, the output of the amplifier 41 is applied through a resistor 46 and a tapped delay line 49 to an inverter buffer amplifier 51. The delay line 49 produces a delay equal to the period of one-half the carrier ripple, or in other words, one-forth the ultrasonic frequency of the sonic pulses. The resistor 46 matches the amplifier with the characteristic impedance of the delay line. The amplifier 51 produces the waveform 53 at the output thereof in response to the input waveform 31.

It will be noted that the excursions of the waveform 47 correspond to the cross hatched areas 33 and 35 in FIG. 2 except they are inverted. Thus, by adding the waveform 47 to the input waveform, a step function can be closely approximated. This property of the differentiated waveform 47 accounts for the success of the present invention. The output of the differentiator 45 as represented by the waveform 47 is added to the output signal of the buffer amplifier 51 through summing resistors 55 and 57 and are amplified by the mixer amplifier 58 and the inverting buffer amplifier 59. The resistor 57 is shunted by a capacitor 56 to ensure good rise time for the output signal of the differentiator 45 when added to the output of the buffer amplifier 51. The resulting output signal that is produced is the waveform 60, which, as can be seen, more closely approximates a stepped waveform than the input waveform 44. Because the carrier ripple is shifted 180 degrees between summing signals as a result of the delay provided by the delay line 49, the carrier signal is nearly completely cancelled. The steep positive going rise of the waveform 47 fills in the slow rise of the waveform 53 thereby correcting the rise time for a near step function response. The steep negative fall of the waveform 47 is subtracted from the slow fall of the waveform 53 thereby correcting the fall time also for a near step function response. The inverting buffer amplifier 59 restores the polarity of the signal to be the same sense as the input signal.

The buffer amplifier 51 comprises a differential amplifier 72 having its positive input connected to ground through a resistor 75 and having its output connected to its negative input through a parallel circuit of a capacitor 79 and a resistor 77. The output of the delay line 49 is connected to the negative input of the differential amplifier 72 through a resistor 80. Resistors 77 and 80 determine the gain of the buffer amplifier. The resistor 77 and the capacitor 79 determine the high frequency roll-off and ensure stability of the buffer amplifier. Resistor 75 serves to balance the input currents to the differential amplifier 72.

The output signal from the amplifier 41 is applied in the differentiator 45 through a series circuit of a resistor 83 and a capacitor 85 to the negative input of a differential amplifier 81. The positive input of the differential amplifier 81 is connected to ground through a resistor 87, which balances the input current to the differential amplifier 81. The output of the differential amplifier 81 is connected to the negative input thereof through a parallel circuit of a resistor 84 and a capacitor 91. In the differentiator 45, the resistors 83 and 84 and the capacitors 85 and 91 determine the high frequency roll-off characteristics and the resistor 84 and the capacitor 85 determine the low frequency roll-off characteristics. The output from the differential amplifier 81 is connected to ground through the resistance of a potentiometer 92, the movable tap of which is connected through the summing resistor 57 to the input of the mixer amplifier 58. The potentiometer 92 serves as a means for adjusting the amplitude of the correction signal added to the output of the buffer amplifier 51 so as to precisely achieve the desired step function.

In the buffer amplifier 58, the summed outputs of the buffer amplifier 51 and the differentiator 45 are applied to the negative input of a differential amplifier 98. The positive input of the differential amplifier 98 is connected to ground through a resistor 99 which balances the input currents for the differential amplifier 98. The output of the differential amplifier 98 is connected to the negative input through a parallel circuit of a resistor 101 and a capacitor 103. The resistor 101 determines the gain for the amplifier 58 and together with the capacitor 103 determines the high frequency roll-off characteristics for the amplifier 58 and ensures stability.

Because of the action of the circuit illustrated in FIG. 3, each reflection is represented by a pulse having a steep rise and fall approximating a step waveform and the carrier ripple is substantially eliminated. As a result, a great enhancement of the image stored in the image storage device is achieved. The improvement is obtained because sharper rise and fall times of the image producing signal give greater contrast to the grey level in the image at the boundary points in the image. An image generated by the waveform 31 of FIG. 2 would not sharply define a boundary of the structure giving rise to it, but would appear rather fuzzy and unclear at the corresponding boundary point. If another echo signal follows closely, it would tend to ride on the preceeding signal's fall time thus creating a false amplitude for itself and causing the preceeding echo signal to fail to restitute. The resulting image generated would have a filled in appearance suggesting tissue boundary conditions where in fact none actually exist. The improvement of image quality is most noticeable when soft tissue is being observed such as the placent or liver tissue where there are a great many rapidly occurring low level signals being reflected. The signal processing technique provided by the present invention produces higher resolution and a crisper, more detailed, more complete and more diagnostic image.

I claim:

1. In an ultrasonic scanning device having means to apply ultrasonic pulses to a subject to scan impedance changes in said subject and to detect the resulting sonic reflections and generate electrical signals from said reflections and a receiver to demodulate the received signals, the improvement wherein there is provided differentiating means to differentiate the output signal of said receiver to provide a differential signal and summation means to add said differential signal to a representation of the output signal of said receiver to provide a summation signal.

2. An ultrasonic scanning system as recited in claim 1, wherein there is provided circuit means to delay the output of said receiver by one-half cycle of the ripple frequency in the receiver output caused by the carrier frequency of the sonic pulses in order to shift said representation of the output signal of said receiver by one-half cycle of said ripple frequency relative to said differential signal.

3. In an ultrasonic scanning system as recited in claim 2, wherein said differentiating means inverts the signal applied thereto and wherein said circuit means receives the same input signal applied to said differentiator and includes means to invert the signal received thereby.

4. An ultrasonic scanning system as recited in claim 1, wherein there is provided means to adjust the amplitude of said differential signal relative to said representation of the output signal of said receiver.

5. A signal processor for use in an ultrasonic scanning or imaging system comprising differentiating means for differentiating the signal applied to the input thereof to provide a differential signal, circuit means for providing a delayed representation of the signal applied to the input thereof, input means for receiving an input signal and applying a representation of said input signal to the input of said differentiating means and the same representation of said input signal to the input of said circuit means, and summing means for adding said differential signal to said delayed representation.

6. A signal processor as recited in claim 5, wherein there is provided means to adjust the amplitude of said differential signal.

7. A signal processor as recited in claim 5, wherein said differentiator inverts the signal applied to the input thereof, and wherein said circuit means includes means to invert the signal applied to the input of said circuit means.

8. In an ultrasonic imaging device having means to apply ultrasonic pulses to a subject to scan impedance changes in said subject and to detect the resulting sonic reflections and generate electrical signal from said reflections, and a receiver to demodulate the received signals, and an image storage device to store an image of the acoustic impedance changes represented by said electrical signals, the improvement wherein there is provided differentiating means to differentiate the output signal of said receiver to provide a differential signal and summation means to add said differential signal to a representation of the output signal of said receiver to provide a summation signal, and means to apply said summation signal to said image storage device to provide said image of said acoustic impedance changes.

9. An ultrasonic imaging system as recited in claim 8, wherein there is provided circuit means to delay the output of said receiver by one-half cycle of the ripple frequency in the receiver output caused by the carrier frequency of the sonic pulses in order to shift said representation of the output signal of said receiver by one-half cycle of said ripple frequency relative to said differential signal.

10. In an ultrasonic imaging system as recited in claim 9, wherein said differentiating means inverts the signal applied thereto and wherein said circuit means receives the same input signal applied to said differentiator and includes means to invert the signal received thereby.

11. An ultrasonic imaging system as recited in claim 8, wherein there is provided means to adjust the amplitude of said differential signal relative to said representation of the output signal of said receiver.

* * * * *